US010420520B2

(12) United States Patent
Fu (10) Patent No.: US 10,420,520 B2
(45) Date of Patent: Sep. 24, 2019

(54) X-RAY IMAGING APPARATUS

(71) Applicant: KONINKLIJKE PHILIPS N.V., Eindhoven (NL)

(72) Inventor: Yan Ning Fu, Suzhou (CN)

(73) Assignee: KONINKLIJKE PHILIPS N.V., Eindhoven (NL)

(*) Notice: Subject to any disclaimer, the term of this patent is extended or adjusted under 35 U.S.C. 154(b) by 90 days.

(21) Appl. No.: 15/504,242

(22) PCT Filed: Aug. 17, 2015

(86) PCT No.: PCT/EP2015/068865
§ 371 (c)(1),
(2) Date: Feb. 15, 2017

(87) PCT Pub. No.: WO2016/026817
PCT Pub. Date: Feb. 25, 2016

(65) Prior Publication Data
US 2017/0258416 A1    Sep. 14, 2017

(30) Foreign Application Priority Data

Aug. 19, 2014 (WO) ................ PCT/CN2014/084700
Nov. 7, 2014 (EP) .................................... 14192201

(51) Int. Cl.
*A61B 6/00* (2006.01)
*A61B 6/08* (2006.01)
(Continued)

(52) U.S. Cl.
CPC .............. *A61B 6/08* (2013.01); *A61B 6/0407* (2013.01); *A61B 6/06* (2013.01); *A61B 6/4429* (2013.01); *A61B 6/547* (2013.01); *A61B 6/44* (2013.01)

(58) Field of Classification Search
CPC ........ A61B 6/4429; A61B 6/547; A61B 6/585
See application file for complete search history.

(56) References Cited

U.S. PATENT DOCUMENTS 4,087,694 A    5/1978 Hellstrom
4,139,776 A    2/1979 Hellstrom
(Continued)

FOREIGN PATENT DOCUMENTS

JP    S6468603 A    3/1989
JP    2011125544 A    6/2011
WO    2012147122 A1    1/2012

*Primary Examiner* — Dani Fox
(74) *Attorney, Agent, or Firm* — Larry Liberchuk (57) ABSTRACT

An X-ray imaging apparatus is provided. The X-ray imaging apparatus (100) comprising: an X-ray source unit (101) including an X-ray source for emitting an X-ray beam, the X-ray source unit being movable such that the X-ray beam to be emitted is movable along an axis (X); an X-ray detecting unit (102) comprising an X-ray detector (12) for detecting the X-ray beam, the X-ray detecting unit (102) being movable along the axis (X); and a control unit (105) adapted to control the movement of the X-ray detecting unit (102) in response to a movement of the X-ray source unit (101); wherein the X-ray source unit (101) further includes a laser for emitting a laser beam (La) for indicating a center of the X-ray beam along the axis (X); the X-ray detecting unit (102) further comprises a plurality of sensors (104) arranged along the X-axis (X), each of the plurality of sensors (104) being configured to sense the laser beam (La) and to generate a sensor signal (S, S2, S3, S4, S) indicative of its sensing of the laser beam (La); and the control unit (105) is adapted to control the movement of the X-ray detecting unit (102), based on the sensor signals (S, S2, S3, S4, S) generated by the plurality of sensors.

12 Claims, 8 Drawing Sheets

(51) Int. Cl.
*A61B 6/04* (2006.01)
*A61B 6/06* (2006.01)

(56) References Cited

U.S. PATENT DOCUMENTS

| | | |
|---|---|---|
| 2004/0105526 A1 | 6/2004 | Zhang |
| 2006/0109958 A1* | 5/2006 | Ertel ........................ A61B 6/08 378/205 |
| 2008/0165933 A1 | 7/2008 | Hornig |
| 2011/0249793 A1 | 10/2011 | Lalena |

* cited by examiner

X-RAY IMAGING APPARATUS

CROSS-REFERENCE TO PRIOR APPLICATIONS

This application is the U.S. National Phase application under 35 U.S.C. § 371 of International Application No. PCT/EP2015/068865, filed on Aug. 17, 2015, which claims the benefit of CN Application No. PCT/CN2014/084700, filed on Aug. 19, 2014 and EP Application No. 14192201.3, filed on Nov. 7, 2014. These applications are hereby incorporated by reference herein.

FIELD OF THE INVENTION

The present invention generally relates to an X-ray imaging apparatus, more particularly to an X-ray imaging apparatus which eliminates the need for conventional mechanical coupling between a detector and an X-ray source.

BACKGROUND OF THE INVENTION

During X-ray imaging, it is required that an X-ray detector is always centered with respect to an X-ray beam from an X-ray source. For this reason, a conventional X-ray imaging apparatus may be provided including an X-ray source and an X-ray detector mechanically coupled to each other. Due to the mechanical coupling between the X-ray source and the X-ray detector, the X-ray detector may automatically follow the motion of the X-ray source and thus is always centered with respect to an X-ray beam from the X-ray source. However, as the mechanical coupling may limit relative motion between the X-ray source and the X-ray detector, the X-ray detector may not follow the rotation of the X-ray source and thus the apparatus cannot be used in those cases where the X-ray source is rotated; meanwhile, in such an apparatus, the height of a table on which a subject is disposed cannot be varied since the X-ray detector is usually attached to the table and thus the table's motion may be limited by the mechanical coupling also.

Another kind of X-ray imaging apparatus provides a non-mechanical coupling between an X-ray source and an X-ray detector. In this case, a laser is used for sensing the position and translation of the X-ray source, and a microcontroller is used for generating a control signal in accordance with the sensed position and translation to translate the X-ray detector so as to be always centered with respect to an X-ray beam from the X-ray source. However, the apparatus needs to incorporate a comparatively complex optical detecting system to sense the position and translation of the X-ray source unit and perform complex computations using the microcontroller to convert the sensed position and translation into a control signal for translating the X-ray detector.

US 2006/109958 A1 presents a method and system of aligning an x-ray detector and x-ray tube for data acquisition. The x-ray detector and x-ray tube are equipped with transmitters and receivers designed to provide feedback relating to the orientation, spacing, and general position thereof so as to assist the user to manually position the x-ray tube and x-ray detector relative to one another for data acquisition.

US 2004/105526 A1 presents a digital radiographic imaging system includes an offset table for determining mechanical and structural offsets which would, if not corrected, misalign the source and detector during use. Such offset table is used for calibration of the alignment between the source and detector.

SUMMARY OF THE INVENTION

Therefore, it would be desirable to provide an X-ray imaging apparatus which eliminates the above limitations caused by a mechanical coupling between an X-ray source and an X-ray detector, while enabling the X-ray detector to track the motion or movement of the X-ray source and thus to be centered with respect to an X-ray beam to be emitted from the X-ray source. It would be further desirable that said X-ray imaging apparatus is of comparatively simple configuration and the track of the motion or movement of the X-ray source does not require a microcontroller.

In accordance with an embodiment of the present invention, there provides an X-ray imaging apparatus comprising an X-ray source unit including an X-ray source for emitting an X-ray beam towards a subject, the X-ray source being movable so as to irradiate different regions of the subject, an X-ray detector for detecting the X-ray beam, the detector being movable in response to a movement of the X-ray source and a control unit adapted to control a movement of the X-ray detector, wherein the X-ray source unit includes a laser for emitting a laser beam towards the X-ray detector, the detector comprising a plurality of sensors for sensing the laser beam and generating a plurality of sensor signals indicative of a position of the X-ray detector with respect to the X-ray source unit, the control unit being adapted to control the movement of the X-ray detecting unit based on the plurality of sensor signals.

In accordance with an embodiment of the present invention, there provides an X-ray imaging apparatus comprising: an X-ray source unit, an X-ray detecting unit and a control unit. The X-ray source unit includes an X-ray source for emitting an X-ray beam, and the X-ray source unit is movable such that the X-ray beam to be emitted is movable along an axis. The X-ray detecting unit comprises an X-ray detector for detecting the X-ray beam, and the X-ray detecting unit is movable along the axis. The control unit is adapted to control the movement of the X-ray detecting unit in response to a movement of the X-ray source unit. The X-ray source unit further includes a laser for emitting a laser beam for indicating a center of the X-ray beam along the axis; the X-ray detecting unit further comprises a plurality of sensors arranged along the X-axis with each of the plurality of sensors being configured to sense the laser beam and to generate a sensor signal indicative of its sensing of the laser beam; and the control unit is adapted to control the movement of the X-ray detecting unit, based on the sensor signals generated by the plurality of sensors.

The sensor signal may indicate whether the laser beam is received by the corresponding sensor. In an example, the sensor signal can be a binary signal representing whether the laser beam is received by the corresponding sensor. In another example, the sensor signal can represent the magnitude of the laser beam sensed by the sensor.

The person skilled in the art would appreciate that the movement of a beam such as the X-ray beam along the axis means that the region illuminated by the beam moves along the axis. There are various ways to move the X-ray beam to be emitted along the axis. In an example, the X-ray source unit translates along the axis such that the X-ray beam also translates and thus moves along the axis. In another example, the X-ray source unit rotates about a further axis orthogonal to the axis such that the X-ray beam moves along the axis.

In accordance with the above embodiment of the present invention, when the X-ray source unit is moved such that the X-ray beam to be emitted toward the X-ray detection unit moves in a direction along the axis, the laser beam emitted toward the X-ray detection unit and indicating the center of the X-ray beam correspondingly moves in the same direction along the axis and thus illuminates different sensors of the plurality of sensors, resulting in a change of the sensor signals. In other words, the change of the sensor signals indicates the movement of the X-ray beam to be emitted. Thus, by using the sensor signals, the control unit can automatically control the movement of the X-ray detecting unit to achieve an alignment between the X-ray beam and the X-ray detector. For example, the control unit may be configured to move the X-ray detecting unit in such a way that the center of the X-ray beam to be emitted is align with the center of the X-ray detector.

In a further embodiment of the present invention, the plurality of sensors include at least a first set of sensors located at, or adjacent to, a center of the X-ray detector along the axis; and the control unit is adapted to stop the movement of the X-ray detecting unit if the sensor signals generated by the plurality of sensors indicate that the laser beam is received by at least one of the first set of sensors. The person skilled in the art would appreciate that the center of the X-ray detector shall be construed as the center of the X-ray sensitive region of the X-ray detector. In a further embodiment of the present invention, the plurality of sensors further include a second and a third set of sensors located, respectively, at a first side and a second side of the first set of sensors; the control unit is adapted to move the X-ray detecting unit towards the first side if the sensor signals generated by the plurality of sensors indicate that the laser beam is received by at least one of the second set of sensors and to move the X-ray detecting unit towards the second side if the sensor signals generated by the plurality of sensors indicate that the laser beam is received by at least one of the third set of sensors.

Each of the first, second and third set of sensors may comprise one or more sensors arranged along the axis.

In a preferred embodiment of the present invention, there provides an X-ray imaging apparatus comprising:

an X-ray source unit including an X-ray source for emitting an X-ray beam, and a laser adapted to emit a laser beam, the laser beam being used for indicating center position(s), along an axis (X), of a region of a subject over which the X ray beam to be emitted by the X-ray source radiates, the X-ray source unit being adapted to be movable such that the laser beam points at different positions along the axis during motion of the X-ray source unit;

an X-ray detecting unit adapted to be movable along the axis in response to motion of the X-ray source, the X-ray detecting unit comprising an X-ray detector for detecting the X-ray beam; and a control unit adapted to control motion of the X-ray detecting unit in response to the motion of the X-ray source unit;

the X-ray imaging apparatus being characterized in that the X-ray detecting unit further comprises a plurality of sensors arranged in a straight line along the axis and fixedly disposed with respect to the X-ray detector, and the plurality of sensors is adapted to sense the laser beam from the laser and generate a plurality of sensor signals each of which is generated by a corresponding sensor of the plurality of sensors, the plurality of sensors being adapted to be movable together with the X-ray detector along the axis, and the plurality of sensors comprising a first set of sensors located at or adjacent to a center of the X-ray detector and a second and a third set of sensors located at a first side and a second side, respectively, relative to the center of the X-ray detector, the center of the X-ray detector being indicative of a center of the X ray detector along the axis (X); and the control unit is adapted to control the motion of the X-ray detecting unit, based on the plurality of sensor signals.

According to one or more of the above embodiments of the present invention, a plurality of sensors for sensing a laser beam emitted from the X-ray source unit and for positioning the X-ray beam to be emitted is provided together with the X-ray detector for detecting the X-ray beam in the X-ray detector unit along the axis X. The plurality of sensors may be divided into individual sets and generate a plurality of sensor signals when the laser beam is emitted. Based on the plurality of sensor signals, the control unit may determine the position at which the laser beam is pointing on the X-ray detecting unit along an X axis. This may be approximately achieved by determining a set of sensors comprising a sensor which accurately receives the laser beam. After that, the control unit may control the X-ray detecting unit so as to move in a corresponding direction, based on the sensor signals. In this way, the X-ray detecting unit may be automatically moved to track the motion of the X-ray source unit until the X-ray detecting unit is centered with respect to the laser beam, i.e., the X-ray beam to be emitted. After the X-ray detecting unit is moved to a position at which it is centered with respect to the laser beam, the X-ray imaging apparatus may perform an imaging procedure by emitting an X-ray beam by the X-ray source of the X-ray source unit and receiving the X-ray beam by a detector of the X-ray detecting unit. There is no need any more for mechanical coupling between the X-ray detecting unit and the X-ray source unit. Therefore, it may be applicable in cases where the X-ray source unit is rotated or the height of a table for supporting a subject is varied.

In one embodiment of the present invention, the control unit of the X-ray imaging apparatus is adapted to control the X-ray detecting unit to move towards the first side if the plurality of sensor signals indicate that the laser is emitting the laser beams towards the second set of sensors, and to move towards the second side if the plurality of sensor signals indicate that the laser is emitting the laser beams towards the third set of sensors, and said control unit is adapted to stop the movement of the X-ray detecting unit (i.e. to control the movement of the X-ray detecting unit to stop moving) if the plurality of sensor signals indicate that the laser is emitting the laser beams towards the first set of sensors.

In another embodiment, each of the second and third set of sensors comprises a first subset of sensors and a second subset of sensors, respectively, the first subsets of sensors of the second and third set of sensors being located away from the center of the X-ray detector relative to the second subsets of sensors of the second and third set of sensors. In this case, the control unit is adapted to control the X-ray detecting unit to move at a first speed if the plurality of sensor signals indicate that the laser is emitting the laser beams towards a first subset of sensors, and at a second speed if the plurality of sensor signals indicate that the laser is emitting the laser beams towards a second subset of sensors, wherein the first speed is higher than the second speed.

In another embodiment, each of the second and third set of sensors comprises a first subset of sensors and a second subset of sensors, and the first subsets of sensors of the second and third set of sensors are located away from the first set of sensors relative to the second subsets of sensors of the second and third set of sensors; and the control unit is adapted to control the X-ray detecting unit to move at a first speed if the sensor signals generated by the plurality of sensors indicate that the laser beam is received by at least one of the first subset of sensors and to move at a second speed if the sensor signals generated by the plurality of sensors indicate that the laser beam is received by at least one of a second subset of sensors, and the first speed is higher than the second speed.

Since the first subset of sensors is located farther away from the center of the detector as compared to the second subset of sensors, the X-ray detecting unit need to move for a longer distance before being aligned to the X-ray source unit in a case where the first subset of sensors receives or illuminated by the laser beam as compared to a case where the second subset of sensors receives or illuminated by the laser beam. By moving the X-ray detecting unit at a higher speed when it is farther way from the destination (i.e. the position where the X-ray source unit and the X-ray detection unit are aligned with each other), it can shortened the time required to move the X-ray detection to the destination. By moving the X-ray detecting unit at a lower speed when it is near to the destination, it is easy to stop the X-ray detecting unit at the destination, In light of the above embodiments, a moving orientation and/or speed of the X-ray detecting unit may be controlled to track the motion of the X-ray source. In particular, the moving speed of the X-ray detecting unit will be reduced gradually as the laser beam is getting closer to the set of sensors located at or adjacent to the center of the X-ray detector. Therefore, the motion of the X-ray detecting unit may be accurately controlled.

In another embodiment, the laser is an infrared laser and the plurality of sensors are infrared receivers. The infrared laser and the infrared receivers may be easily commercially obtained and the costs thereof are relatively low.

In a further embodiment, the laser is a modulated laser which emits laser beams modulated at a predetermined frequency, and the control unit further comprises a plurality of band filters each of which is used for filtering a corresponding sensor signal of the plurality of sensor signals, each of the band filters having a center frequency equal to the predetermined frequency. Since only a sensor signal indicative of the modulated laser beam may pass the band filter, the negative impact of ambient noise will be reduced.

In a still further embodiment, the plurality of sensors is arranged on a detector carrier in which the X-ray detector is mounted. For example, the plurality of sensors may be attached to one side of the X-ray detector on the detector carrier. Please note that the plurality of sensors may not be blocked by a table for supporting a subject to be imaged such that the plurality of sensors (104) can sense the laser beam (La) from the laser. Therefore, the X-ray detecting unit of the X-ray imaging apparatus may be easily obtained.

In a further embodiment, the X-ray imaging comprises a user interface for outputting an indicating signal if none of the plurality of sensor signals is higher than a second predetermined threshold. Alternatively, the user interface is configured to output an indicating signal if an indicating signal if the sensor signals generated by the plurality of sensors indicate that the laser beam (La) is received by none of the plurality of the sensors.

In a further aspect, there are different configurations for the control unit of the X-ray imaging apparatus, wherein the control unit may be achieved in a microcontroller-free manner. Therefore, there is no need for complex computation.

According to an embodiment of the present invention, the control unit is adapted to generate a control signal, based on the plurality of sensor signals ($S_1$, $S_2$, $S_3$, $S_4$, $S_5$), and output the same to a motor for driving the motion of the X-ray detecting unit.

In one embodiment, the control unit comprises a plurality of comparators, each of which is adapted to receive a corresponding sensor signal of the plurality of sensor signals as a first input and a first predetermined threshold as a second input, to compare a magnitude of the corresponding sensor signal with the first predetermined threshold, and to output a comparing result as an output; and the control unit is further adapted to generate the control signal, based on comparing results obtained, respectively, from the plurality of comparators.

It is preferred that the first predetermined threshold is a weighted average of magnitudes of the plurality of sensor signals. To achieve this, the ambient lights sensed by the plurality of sensors together with the laser beam may be considered.

In another embodiment, the control unit further comprises a plurality of switching circuits, each of which receives comparing results of corresponding comparators of the plurality of comparators, the corresponding comparators comparing corresponding sensor signals from a first sensor and a second sensor, respectively, with the first predetermined threshold to derive the comparing results, wherein the first sensor and the second sensor are from different sets of sensors located at a same side relative to the center of the X-ray detector, and wherein the second sensor is located adjacent to the center of the X-ray detector relative to the first sensor, or the second sensor being from the first set of sensors located at or adjacent to the center of the X-ray detector.

In this case, each of a plurality of switching circuits is configured to be switched off to invalidate or disable a comparing result derived by comparing a sensor signal from the first sensor with the first predetermined threshold when the comparing results from the corresponding comparators indicate that both magnitudes of the sensor signals from the first sensor and second sensor are larger than the first predetermined threshold, so that the control signal is generated based on a comparing result derived by comparing the sensor signal from the second sensor with the first predetermined threshold.

In this embodiment, if more than one sensor of different sets of sensors, respectively, generate sensor signals indicating that a laser is emitting a laser beam towards them, then the control unit may control an X-ray detecting unit 102 to move at a relatively low speed corresponding to one of the different sets of sensors. This may simplify the operation of tracking the X-ray detecting unit to the X-ray source unit in a noisy environment.

Moreover, the control unit is adapted to generate a pulse-suppressing signal for suppressing the motion of the X-ray detecting unit when the plurality of sensor signals indicate that the emitted laser beam is moved from the first subset of sensors to the second subset of sensors. In this way, the speed of motion of the X-ray detecting unit may be reduced by switching from a relatively high speed to a relatively low speed. Therefore, the motion of the X-ray detecting unit may be accurately controlled.

In accordance with another aspect of the present invention, there provides an X-ray imaging method comprising:

receiving a laser beam emitted from an X-ray source unit, the laser beam indicating center position(s), along an axis, of a region of a subject over which the X-ray beam to be emitted by the X-ray source radiates, wherein the X-ray source unit comprises an X-ray source for emitting the X-ray beam and a laser adapted to emit the laser beam and to be movable such that the laser beam points at different positions along the axis during motion of the X ray source unit;

generating a plurality of sensor signals by a plurality of sensors being arranged in a straight line along the axis and fixedly disposed with respect to the X-ray detector, the plurality of sensors being adapted to be movable together with an X-ray detector along the axis in response to a motion of the X-ray source unit, each of the plurality of sensor signals being generated by a corresponding sensor of the plurality of sensors, wherein the plurality of sensors comprises a first set of sensors located at or adjacent to a center of the X-ray detector and a second and a third set of sensors located at a first side and a second side, respectively, relative to the center of the X-ray detector; and controlling motion of the X-ray detector along the axis, based on the plurality of sensor signals.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present invention will be described and explained hereinafter in more detail in combination with embodiments and with reference to the drawings, wherein.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 1A:
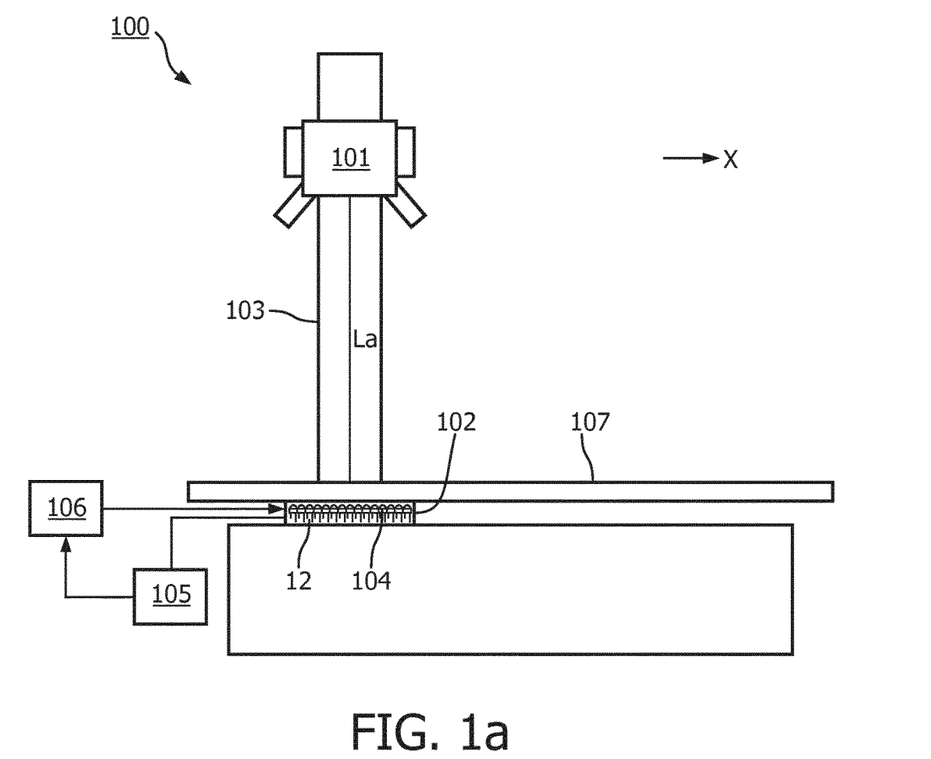
FIGS. 1a and 1b are schematic representations of an X-ray imaging apparatus according to an embodiment of the present invention.
Figure 1B:
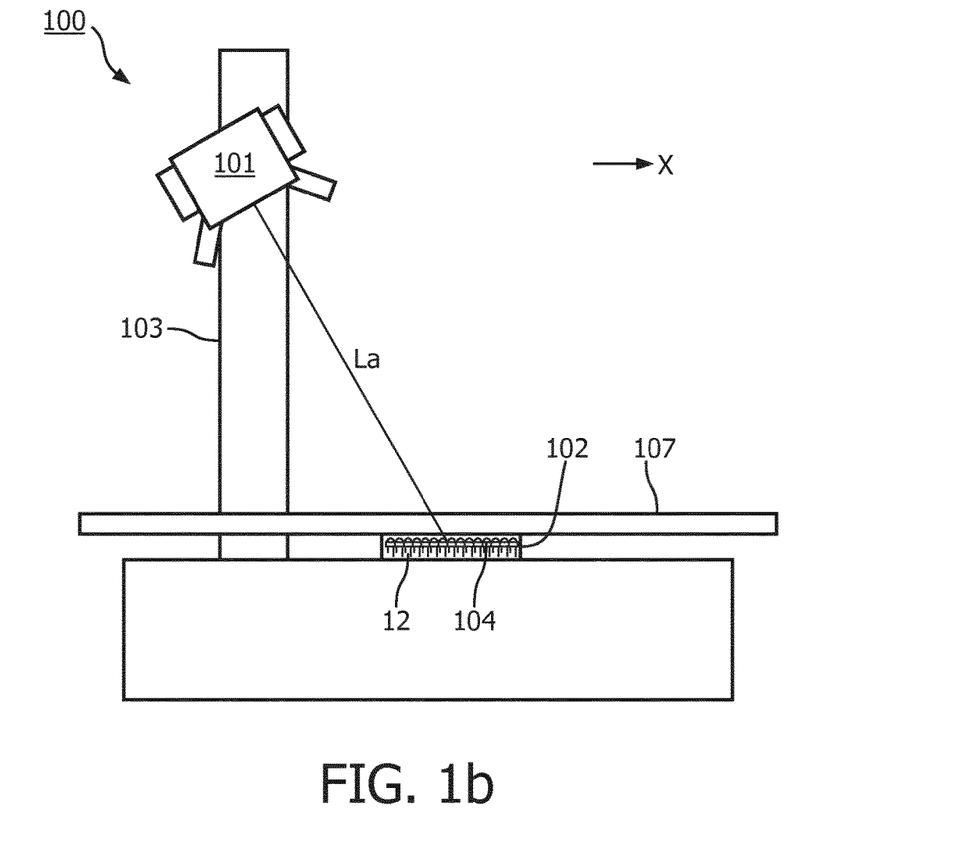

FIGS. 1a and 1b are schematic representations of an X-ray imaging apparatus 100 according to an embodiment of the present invention. The X-ray imaging apparatus 100 comprises an X-ray source unit 101, an X-ray detecting unit 102, a tube stand 103 and a control unit 105. FIG. 1a also shows a motor 106 which receives a control signal from the control unit 105 to drive the X-ray detecting unit 102 to cause it to move in response to motion of the X-ray source unit 101. Please note that although the control unit 105 and the motor 106 are not shown in FIG. 1b, it may be understood that this is only for simplifying the drawings, not for limitation.

The X-ray source unit 101 may comprise an X-ray source for emitting an X-ray beam and a laser fixedly disposed with respect to the X ray source and adapted to emit a laser beam La for positioning the X-ray beam to be emitted from the X ray source. In particular, the laser beam La indicates center position(s), along an X axis, of a region of a subject over which the X-ray beam to be emitted by the X-ray source radiates. The X-ray source unit 101 may be movable such that the laser beam points at different positions along the X axis during the motion of the X-ray source unit 10.

FIG. 1a illustrates a case where the X-ray detecting unit 102 is moved so as to follow the translation of the X-ray source unit 101, and FIG. 1b illustrates the case where the X-ray detecting unit 102 is moved so as to follow the rotation of the X-ray source unit 101. It may be understood that the motion of the X-ray source unit 101 may not be limited to the translation and the rotation only; other types of motions may be contemplated also as long as the motion of the X-ray source unit 101 causes the laser beam emitted therefrom to point at different positions along the X axis during said motion.

Since the laser may move together with the X-ray source, the laser beam La emitted from the laser may always indicate center position(s), along an X axis, of a region of a subject over which the X-ray beam to be emitted by the X-ray source radiates, thereby achieving the positioning of the X-ray beam to be emitted by means of the laser beam. Therefore, a position on an X-ray detector at which the X-ray beam points may be determined by deriving a position on the X-ray detector at which the laser beam points. In an embodiment, the laser may be an infrared laser for emitting an infrared laser beam. More preferably, the laser may be a modulated laser which emits the laser beam modulated at a predetermined frequency.

Although FIGS. 1a and 1b do not show a detailed configuration of the X-ray source unit 101, it will be clear to those skilled in the art. In some instances, the laser may be built in a collimator, and said collimator, which is fixedly disposed with respect to an X-ray source, may be used as the X-ray source unit 101 in other embodiments of the invention.

It may be understood that the laser beam may illuminate towards a table 107 on which a subject may be supported, and form a cross line or a straight line perpendicular to the X axis within a plane of the table.

During an X-ray imaging procedure, the X-ray source unit 101 may be moved, for example translated along the X axis (as shown in FIG. 1a) or rotated in a direction perpendicular to the X axis (as shown in FIG. 1b), to enable that the laser beam points at different positions along the X axis.

The X-ray detecting unit 102 of the X-ray imaging apparatus 100 is different from an X-ray detector 12 of a conventional X-ray imaging apparatus. The X-ray detecting unit 102 includes a plurality of sensors 104 in addition to an X-ray detector 12. The plurality of sensors 104 may be aligned in a straight line along the X axis and fixedly disposed with respect to the X-ray detector 12. The plurality of sensors 104 may be adapted for receiving and sensing the laser beam from the X-ray source unit 101. In particular, each of the plurality of sensors 104 is disposed at a different position along the X axis and at least one of them is located at or adjacent to a center of the X-ray detector 12. In one instance, the sensors may be infrared receivers for sensing an infrared laser beam when the laser is an infrared laser.

Figure 2A:
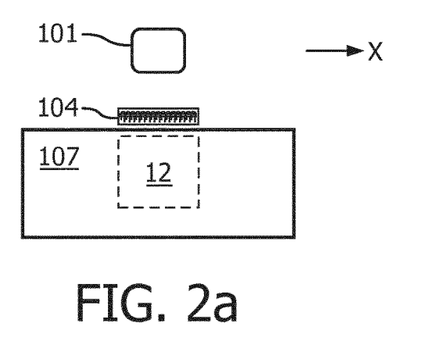
FIGS. 2a, 2b and 2c are a top view, rear view and side view, respectively, of the X ray imaging apparatus according to one embodiment of the present invention.
Figure 2B:
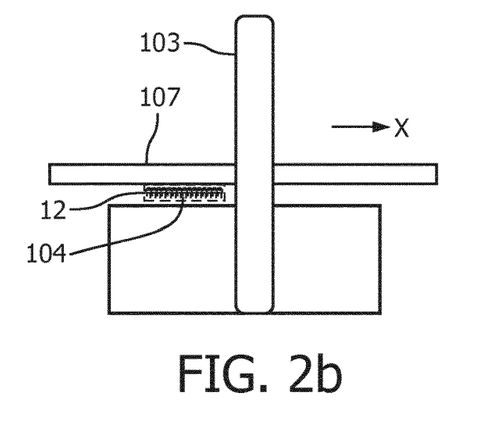
Figure 2C:
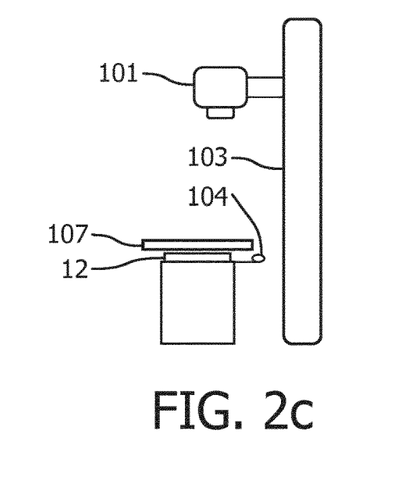

The plurality of sensors 104 has to be disposed such that they are not blocked by a table 107 for supporting a subject to be imaged, to ensure that the plurality of sensors can sense the laser beam from the laser. FIGS. 2a, 2b and 2c are a top view, rear view and side view, respectively, of the X ray imaging apparatus 100 according to one embodiment. As shown in the drawings, the plurality of sensors 104 are disposed along the X axis and are adjacent to, but separate from, the detector 12 to ensure that the plurality of sensors 104 can sense the laser beam from the laser. In particular, the plurality of sensors 104 may be arranged to extend over a region of the table, but still are fixedly disposed with respect to the X ray detector 12 disposed below the table, as shown in FIG. 2c. In this case, the laser beam may form a straight line, as described above, which is perpendicular to the X axis within a plane of the table and which may be extended beyond the plane of the table. In one embodiment, such a configuration may be achieved in a simple manner by arranging the plurality of sensors 104 on a detector carrier in which the X-ray detector 12 is disposed along the X axis.

FIGS. 2a, 2b and 2c only show one embodiment for configuring the X-ray detecting unit 102 of the invention, however, this is not to be construed as a limitation. It may be contemplated to attach the plurality of sensors 104 directly to a side edge of the detector 12 along the X axis, the side being perpendicular to a plane of the table 107, as long as the plurality of sensors 104 can sense the laser beam from the laser, i.e., the table does not block the laser beam to be sensed by the plurality of sensors 104.

As shown in FIGS. 1a and 1b, the X-ray detecting unit 102 may be movable along the X axis in response to motion of the X-ray source unit 101, including translation (FIG. 1a) and rotation (FIG. 1b) of the X-ray source unit 101, to track the motion of the X-ray source unit 101 along the X axis. Although FIGS. 1a and 1b do not show this clearly, it should be noted that there is no need to have mechanical coupling between the X-ray source unit 101 and the X-ray detecting unit 102 according to the invention. In one implementation, the X-ray source unit 101 may be fixed to a ceiling of a room and the mechanical coupling may be omitted. In this configuration, the plurality of sensors 104 may be moved together with the X-ray detector 12 along the X axis in response to the motion of the X-ray source unit 101, since they are integral parts of the X-ray detecting unit 102.

In order to receive an X-ray beam from the X-ray source unit 101, it is desired that the X-ray detecting unit 102 may be automatically centered with respect to the X-ray beam to be emitted from the X-ray source unit 101 when the X-ray source unit moves such that the X-ray beam may impinge on the X-ray detector 12. The plurality of sensors 104 may be used to sense a laser beam for positioning the X-ray beam to be emitted from the X-ray source unit 101 and generate corresponding sensor signals to determine the position of the X-ray beam to be emitted on an X-ray detector 12 by deriving a position at which the laser beam points on the X-ray detector 12. After it is determined that the X-ray detector 12 will be centered with respect to the X-ray beam to be emitted, the X-ray beam may be actually emitted and the X-ray detector 12 may receive the X-ray beam for imaging.

In an embodiment, the plurality of sensors 104 are divided into different sets corresponding to different movement orientations and/or moving speeds of the X-ray detecting unit 102. When a laser beam from the X-ray source unit 101 is received by one sensor of a set of sensors, the sensor may generate a sensor signal to indicate that the laser beam is being emitted towards the set of sensors and then the control unit 105 may control the X-ray detecting unit 102 to adopt a movement orientation and/or a moving speed corresponding to the set of sensors. In particular, the control unit 105 may send a control signal to a motor 106 to move the X-ray detecting unit 102.

Figure 3:
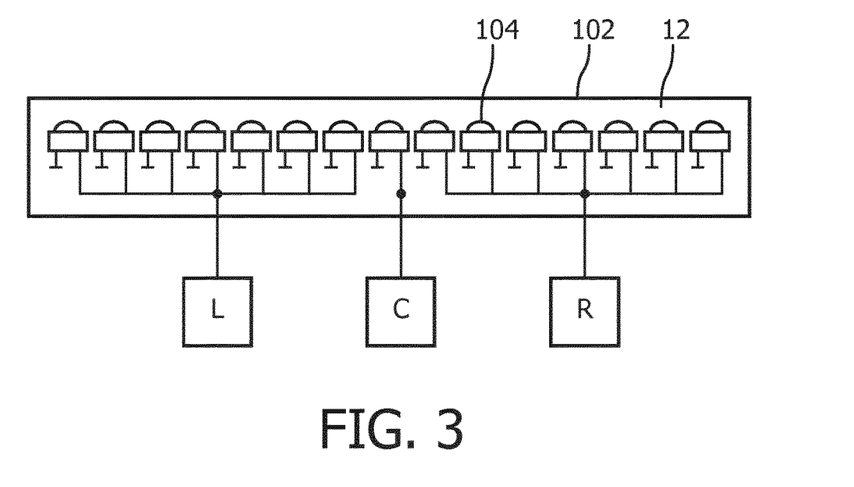
FIG. 3 is a schematic representation of a plurality of sets of sensors to be used in an X-ray imaging apparatus according to the present application.

FIG. 3 illustrates a manner of schematically grouping the plurality of sensors 104. In this embodiment, the plurality of sensors 104 is grouped into three sets of sensors which are indicated by L, C and R, respectively. A first set of sensor(s) C is located at or adjacent to a center of the X-ray detector 12 of the X-ray detecting unit 102. The center of the X-ray detector 12 is defined as a center point of the X-ray detector 12 along the X axis. A second set of sensors L is located at a first side, i.e., the left side, relative to the center of the X-ray detector 12 and a third set of sensors R is located at a second side, i.e., the right side, relative to the center of the X-ray detector 12.

Although FIG. 3 shows that the first sensor set comprises only one sensor and the second and the third sensor sets comprise more than one sensor, those skilled in the art may understand that this is not a limitation, as the first sensor set may comprise more than one sensor also. In particular, the first, second and third sets of sensors may each comprise any number of sensors, if required. However, in order to ensure that the X-ray detector will be centered more accurately with the X-ray beam to be emitted, the number of sensors of the first set of sensors should be as small as possible, preferably one.

When the plurality of sensors 104 are arranged as shown in FIG. 3, the control unit 105 receives the sensor signals, each of which is generated by a corresponding sensor, and determines towards which set of sensors the laser beam, i.e., the X-ray beam, is being emitted. If it is determined from the sensor signals that the laser is emitting the laser beam towards the second set of sensors L located on the first side, i.e., the left side, the control unit 105 controls the X-ray detecting unit 102 to move towards the first side, i.e., the left side. If it is determined from the sensor signals that the laser is emitting the laser beam towards the third set of sensors R located at the second side, i.e., the right side, the control unit 105 controls the X-ray detecting unit 102 to move towards the second side, i.e., the right side. Furthermore, if it is determined from the sensor signals that the laser is emitting the laser beam towards the first set of sensors C, it is indicated that the X-ray detecting unit 102 is centered with respect to the laser beam from the X-ray source unit 101 and thus the control unit 105 may control the X-ray detecting unit 102 to stop its motion. After that, the X-ray source may emit the X-ray beam.

Figure 4A:
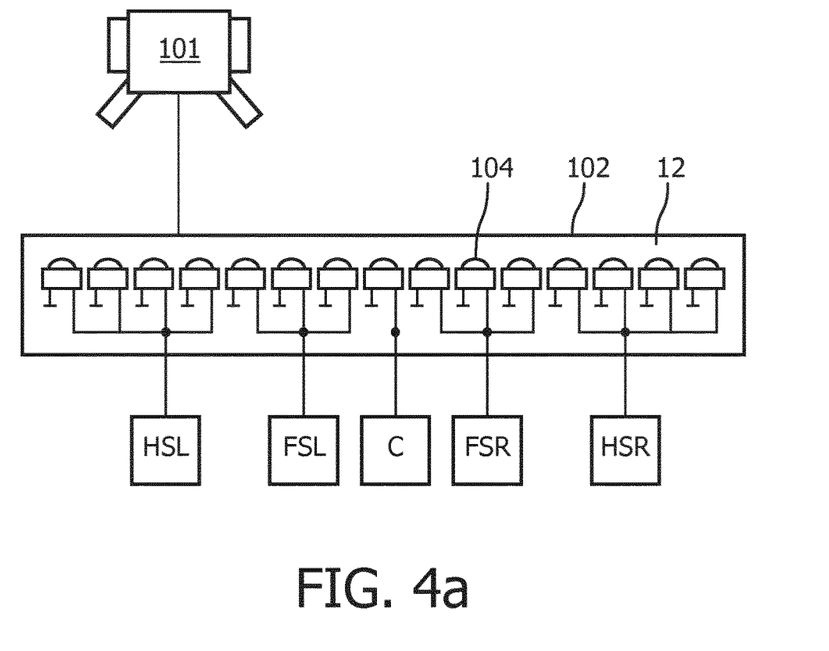
FIGS. 4a and 4b illustrate a plurality of sensors which are shown as five sets of sensors to be used in an X-ray imaging apparatus according to the present application.
Figure 4B:
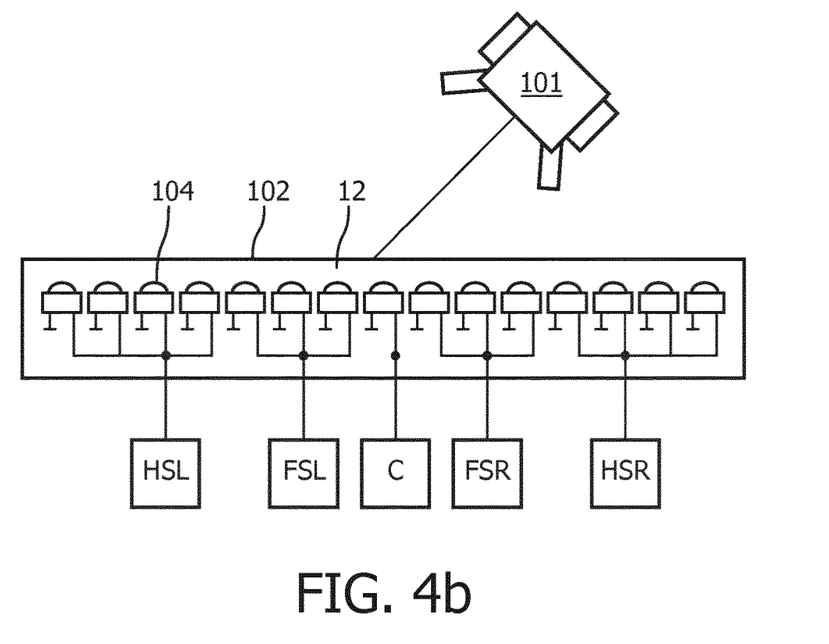

In combination with the manner of grouping the plurality of sensors 104 as shown in FIG. 3, the movement orientation of the X-ray detecting unit 102 may be controlled. FIGS. 4a and 4b show another manner of grouping the plurality of sensors 104 in combination with which the moving speed of the X-ray detecting unit 102 may be controlled also.

As shown in FIGS. 4a and 4b, the second and the third sets of sensors are divided into, or replaced by, two subsets of sensors, respectively, i.e., first subsets of sensors HSL, HSR and second subsets of sensors LSL, LSR. The first subset of sensors HSL of the second set of sensors L and the first subset of sensors HSR of the third set of sensors R are located away from the center of the X-ray detector 12 relative to the second subset of sensors LSL of the second set of sensors L and the second subset of sensors LSR of the third set of sensors R, respectively.

The reference signs HSL, HSR, LSL and LSR represent "high speed and left", "high speed and right", "low speed and left" and "low speed and right", respectively, which indicates the movement orientation and the moving speed of the X-ray detecting unit 102 if the laser is emitting the laser beam towards corresponding sensors. The actual speed of movement corresponding to a different sensor or a different set of sensors may be predetermined or preset on motor 106 by an operator.

As shown in FIG. 4a, the laser beam from the X-ray source unit 101 is pointing at a first subset of sensors HSL. In this case, the control unit 105 determines from the sensor signals that the laser beam, i.e., the X-ray beam, is being emitted towards the first subset of sensors HSL and then the control unit controls the X-ray detecting unit 102 to move towards the first subset of sensors HSL, i.e., the left side, at a high speed. It may be easily understood that if the laser beam from the X-ray source unit 101 is pointing at a first subset of sensors HSR, the X-ray detecting unit 102 may be controlled to move towards the first subset of sensors HSR, i.e. the right side, at a high speed, and if the laser beam from the X-ray source unit 101 is pointing at a second subset of sensors LSL, the X-ray detecting unit 102 may be controlled to move towards the second subset of sensors LSL, i.e. the left side, at a relatively low speed, and if the laser beam from the X-ray source unit 101 is pointing at a second subset of sensors LSR, the X-ray detecting unit 102 may be controlled to move towards the second subset of sensors LSR, i.e. the right side, at a relatively low speed. As shown in FIG. 4b, when the laser beam from the X-ray source unit 101 is pointing at a first set of sensors C, it is indicated that the X-ray detector 12 is centered with respect to the laser beam, as a result of which the X-ray detecting unit 102 is controlled to stop its motion.

With reference to FIGS. 1a, 1b, 4a and 4b, the tracking of the X-ray detecting unit 102 to the motion of the X-ray source according to an embodiment of the present invention has been described. The X-ray imaging apparatus comprises a plurality of sensors 104 incorporated in the X-ray detecting unit 102 to sense the laser beam for positioning the X-ray beam to be emitted, and by determining the orientation and position of a sensor on which the laser beam impinges relative to the center of the X-ray detector 12, the X-ray detecting unit 102 is moved at an orientation and/or speed corresponding to the sensor. Since the X-ray imaging apparatus may derive relative orientation and position by means of the sensor signals, independent of how the X-ray source unit 101 moves, the X-ray imaging apparatus may be applicable to cases where the X-ray source unit 101 rotates, and there is no need for a mechanical coupling between the X-ray source unit 101 and the X-ray detecting unit 102. FIGS. 1b and 4b show cases where the X-ray imaging apparatus is used when the X-ray source unit 101 is being rotated.

It may be contemplated that the closer a set of sensors are placed to the center of the X-ray detector 12, the lower the moving speed of the X-ray detecting unit 102 to which the set of sensor corresponds is. In this way, the tracking of the X-ray detecting unit 102 to the X-ray source may be controlled more accurately when the X-ray beam is close to the center of the X-ray detecting unit 102.

Although the X-ray imaging apparatus has been described with reference to three and five sets of sensors, respectively, it may be understood that any number of sets larger than one are possible.

Furthermore, in order to substantially further reduce the speed of the X-ray detecting unit 102 from a relatively high speed to a relatively low speed, it may be contemplated that the control unit 105 generates a pulse-suppressing signal to suppress the motion of the X-ray detecting unit 102 when the sensor signals indicate that an emitted laser beam has been moved from a set of sensors corresponding to a relatively high speed to another set of sensors corresponding to a relatively low speed. In one implementation, this pulse-suppressing signal may be used to actuate a brake 108, as shown in FIGS. 5 and 6, to temporarily turn off the motor 106.

Next, the configuration of the control unit 105 of the X-ray imaging apparatus is described with reference to FIGS. 5 and 6. The control unit 105 comprises only several discrete electronic components, such as filters, amplifiers and comparators. It is free of microcontrollers and does not need to perform complex computations.

Figure 5:
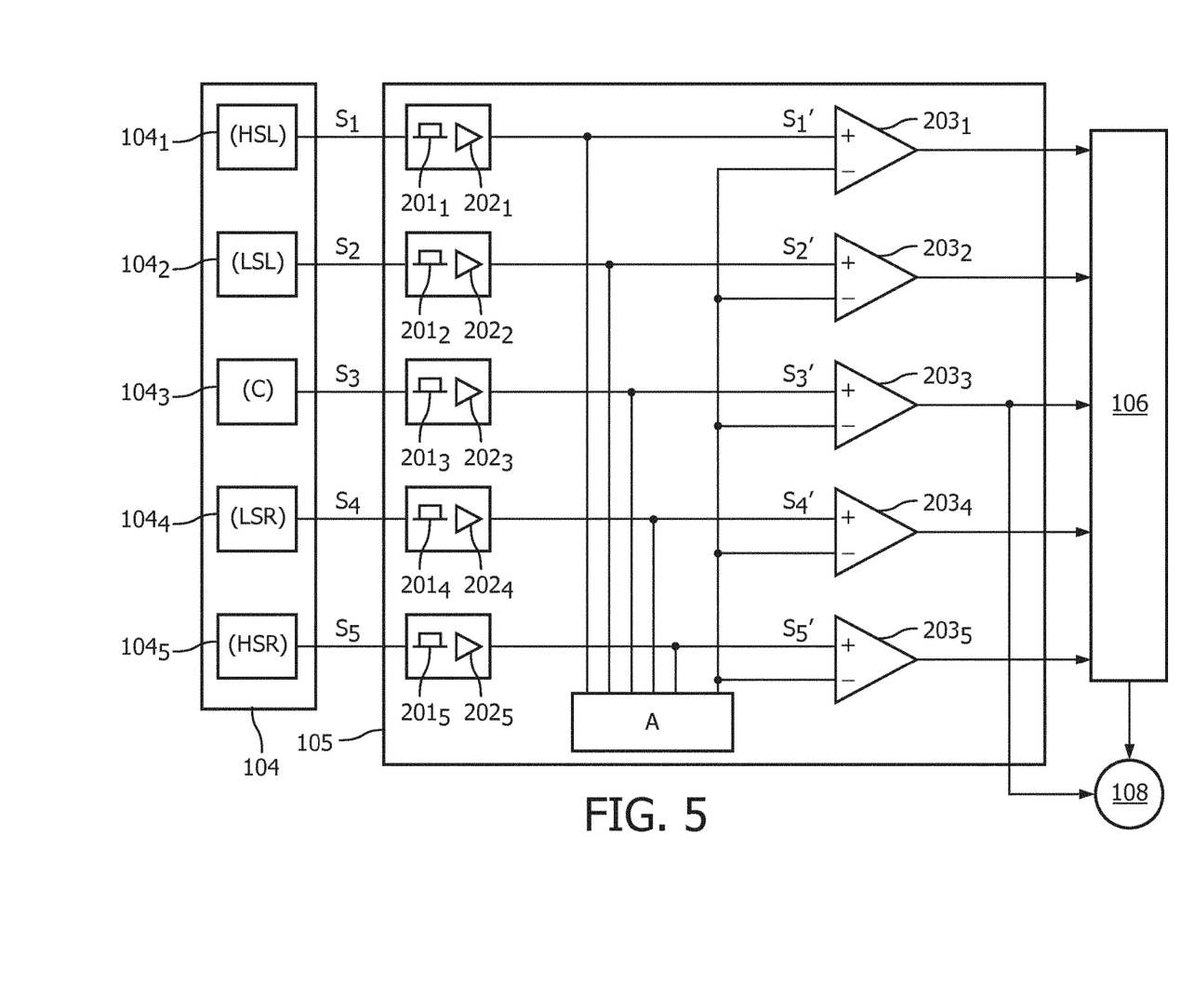
FIG. 5 is a schematic representation of a control unit of an X-ray imaging apparatus according to one embodiment of the present invention.
Figure 6:
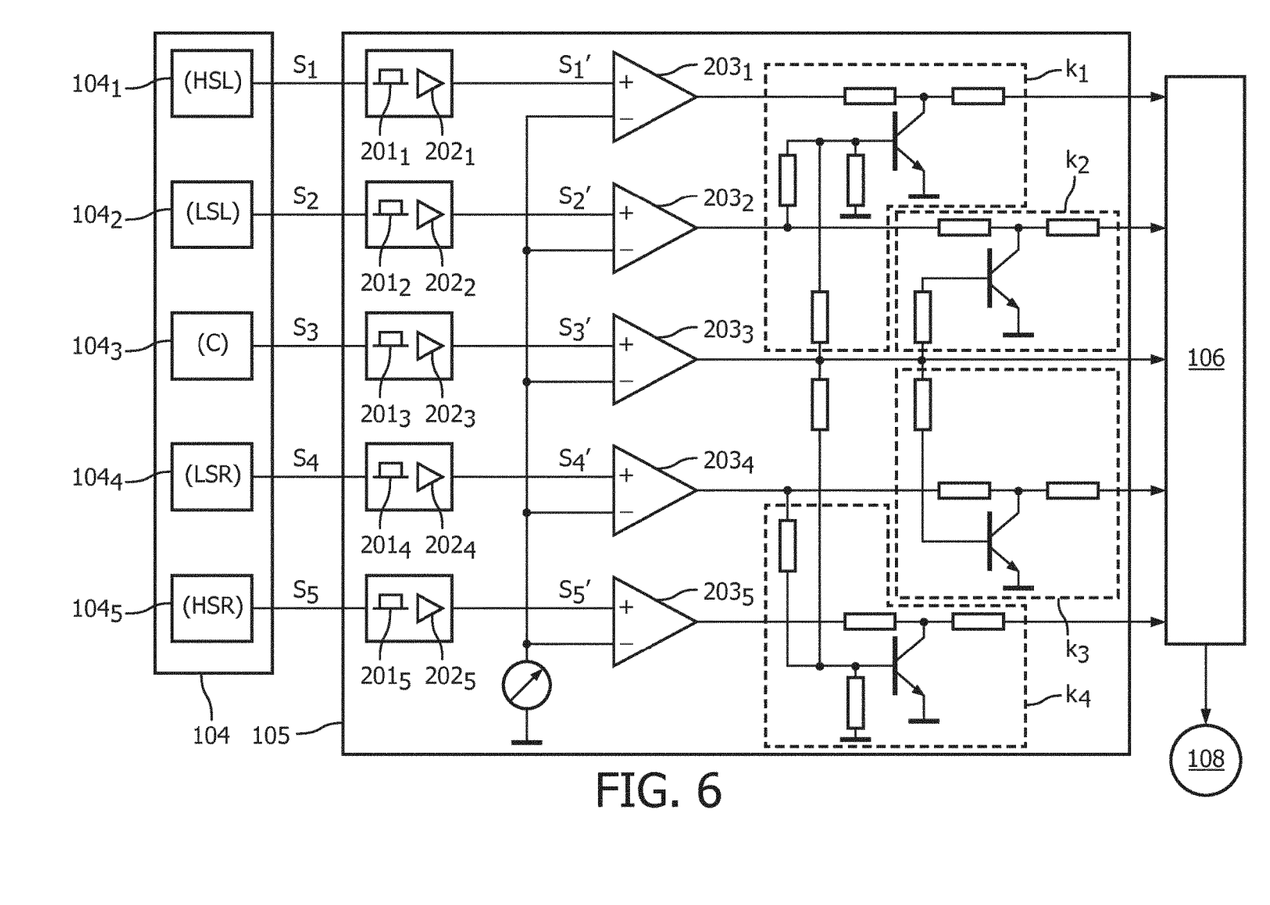
FIG. 6 is a schematic representation of a control unit of an X-ray imaging apparatus according to another embodiment of the present invention.

As shown in FIG. 5, there are five sensors $104_1$-$104_5$, respectively, of the five sets of sensors HSL, LSL, C, LSR, HSR, as described with reference to FIGS. 3a and 3b. A control unit 105a receives sensor signals $S_1$-$S_5$ from the five sensors $104_1$-$104_5$ to generate a control signal based on the plurality of sensor signals and output the same to a motor 106 for driving the motion of the X-ray detecting unit 102. It is preferred, but not required, that each of the sensor signals $S_1$-$S_5$ is subject to band filtering and amplifying, respectively, by means of one of band filters $201_1$-$201_5$ and one of amplifiers $202_1$-$202_5$. The filtered and amplified signals $S_1'$-$S_5'$ may be input as first inputs to corresponding comparators $203_1$-$203_5$. Second inputs of the corresponding comparators $203_1$-$203_5$ may be a predetermined value, which is used as a threshold. In FIG. 5, the threshold is selected to be a weighted average of the magnitudes of the signals $S_1'$-$S_5'$. In particular, the second inputs of the corresponding comparators $203_1$-$203_5$, i.e., the thresholds, are received from a block A, as shown in FIG. 5, in which a weighted average of the magnitudes of the signals $S_1'$-$S_5'$ are derived. The block A represents any electronic component(s), or a combination thereof, which may be used for deriving a weighted average of a plurality of magnitudes. Certainly, other thresholds may be possible also, such as a threshold preset by an operator.

Each of the comparators $203_1$-$203_5$ compares a magnitude of a corresponding signal of the signals $S_1'$-$S_5'$ with the threshold to output a comparing result. The output of each of the comparators $203_1$-$203_5$ are connected to the motor 106. Based on comparing results from the five comparators $203_1$-$203_5$, a control signal is generated for the motor 106 such that the X-ray detecting unit 102 may be moved at a predetermined orientation and/or speed corresponding to the different sensors.

For example, the laser beam from the X-ray source unit 101 is emitted towards a sensor $104_1$ of a set of sensors HSL, and in other words, the laser beam is received by the sensor $104_1$ of a set of sensors HSL, then the magnitude of the signal $S_1'$ may be larger than the threshold and the magnitudes of the signals $S_2'$-$S_5'$ may be smaller than the threshold. In this case, the output of the comparator $203_1$ becomes "valid" or "enabled". The motor 106 is configured to move the X-ray detecting unit 102 toward the left side at a relatively high speed in response to the output of the comparator $203_1$ when the received output of the comparator $203_1$ is "valid" or "enabled", as described above with reference to FIGS. 3a and 3b.

FIG. 6 illustrates another embodiment of the configuration of a control unit 105b of the present application. The control unit 105b differs mainly from the control unit 105a as shown in FIG. 5 in that switching circuits $K_1$-$K_4$ have been incorporated. The switching circuits $K_1$-$K_4$ receive comparing results from corresponding comparators of the comparators $203_1$-$203_5$ as inputs. For example, the comparing results are derived by comparing corresponding sensor signals from a first sensor and a second sensor, respectively, with the predetermined threshold, using the corresponding comparators. The first and second sensors belong to different sets of sensors located at a same side relative to a center of an X-ray detector 12, and the first sensor is located away from the center of the X-ray detector 12 relative to the second sensor. Please note that the second sensor may also belong to the center set of sensors C.

Each of the switching circuits $K_1$-$K_4$ may be configured to be switched off to invalidate or disable a comparing result derived by comparing a sensor signal from the first sensor with the threshold when the comparing results from the corresponding comparators indicate that both magnitudes of the sensor signals from the first sensor and second sensor are larger than the predetermined threshold value, such that the control signal is generated based on a comparing result derived by comparing the sensor signal from the second sensor with the threshold. Therefore, if more than one sensor of different sets of sensors generate sensor signals indicating that a laser is emitting a laser beam towards them, then the control unit 105b may control an X-ray detecting unit 102 to move at a relatively low speed of a plurality of speeds corresponding to the different sets of sensors, or even stop the motion of the X-ray detecting unit 102 when one of the sensors, which generates the sensor signal indicating that a laser is emitting a laser beam towards it, forms part of the center set of sensors C.

The operation of the switching circuits will be described with reference to FIG. 6 below.

A switching circuit $K_2$ is used as an example. The switching circuit $K_2$ comprises several resistors and a triode and receives the comparing results from the comparators $203_2$ and $203_3$ as inputs. The comparing results are obtained by comparing the sensor signals from a first sensor $104_2$ and a second sensor $104_3$, respectively, with a predetermined threshold. In this case, if the comparing results from the comparators $203_2$ and $203_3$ indicate that both the sensor signals $S_2$, $S_3$ from the first sensor $104_2$ and the second sensor $104_3$, respectively, are larger than the threshold, the triode of the switching circuit $K_2$ will drain current from a first branch circuit corresponding to the first sensor $104_2$, thereby invalidating or disabling the output of a comparator from the first branch circuit; therefore, the control unit 105b may control the motor, based on a comparing result from the comparator $203_3$ corresponding to the second sensor $104_3$, to move an X-ray detecting unit 102 in an orientation and a speed corresponding to the second sensor $104_3$, i.e., the control unit 105b may stop the motion of the X-ray detecting unit 102. The other switching circuits may be operated similarly.

Although the operation of the switching circuits is described by referring to a switching circuit $K_2$ which has two comparing results for two comparators, respectively, as inputs, those skilled in the art may understand that the switching circuits may be appropriately modified to receive more than two comparing results as inputs, as shown by a switching circuit $K_1$ and a switching circuit $K_4$ in FIG. 6.

Please note that although FIGS. 5 and 6 show the sensor signals being filtered and amplified before being input to the comparators, those skilled in the art may understand that said filtering and amplifying are not indispensable processes for achieving the tracking of an X-ray detecting unit to an X-ray source.

It may be easily understood that the one or more sensors will receive not only the laser beam but also some ambient lights. In this case, a modulated laser is used. The modulated laser is configured to emit a laser beam modulated at a predetermined frequency, for example 38K HZ, and the control unit 105 comprises corresponding band filters $201_1$-$201_5$, wherein each of the band filters may have a center frequency equal to the predetermined frequency at which a laser beam from a laser has been modulated. In this way, only the sensor signals indicative of the modulated laser beam may pass the band filter for further processing and the sensor signals indicative of the ambient lights only will be blocked; therefore, the ambient noises sensed by the sensors may be eliminated. In this case, since the ambient noises may be eliminated, the threshold will be chosen without considering the noises. In particular, the threshold may be selected to be a comparatively small value but will not affect the function to be achieved by the control unit of, for example, the threshold may be about ½ of the intensity of the input laser signal.

Although FIGS. 5 and 6 only illustrate the case where each set of sensors includes only one sensor, it may be contemplated that each set of sensors includes more than one sensor. In this case, a corresponding comparator (and/or filter and amplifier) may be configured for each of the sensors.

Please also note that although the configuration of the control unit 105 is described with reference to FIGS. 5 and 6, those skilled in the art may conceive other configurations to achieve similar functions. For example, it is possible to design a circuit of the control unit 105 with which a maximum magnitude of the sensor signals may be derived; in this case, the control unit 105 may control the motion of the X-ray detecting unit 102 based on the sensor signal having the maximum magnitude.

Please further note that FIGS. 5 and 6 show the switching circuits $K_1$-$K_4$ according to a preferred embodiment of the invention. However, they are not limitations, as those skilled in the art may be able to conceive a different circuit to achieve similar functions.

Furthermore, it may be contemplated that in accordance with some embodiments of the present invention, the X-ray imaging apparatus comprises a user interface for outputting an indicating signal if the plurality of sensor signals indicate that the laser beam is not received by any of the plurality of sensors. In an embodiment, if none of the plurality of sensor signals is higher than a further threshold, it indicates that the laser beam is not received by any of the plurality of sensors. The indicating signal may be a visual or audio signal. In this manner, an operator may be informed that the laser beam is moving out of a detection range of the plurality of sensors. The operator may manually align an X-ray detector and an X-ray source. The further threshold may be different from the predetermined threshold as described above. In particular, the further threshold may be higher than the predetermined threshold to avoid the X-ray detector being mistakenly moved due to noise signals.

It may also be contemplated that in accordance with some embodiments of the present invention, the X-ray imaging apparatus comprises a manual control button to be used by an operator to manually move the X-ray detecting unit.

Additionally and alternatively, if the plurality of sensor signals indicate that the laser beam is not received by any of the plurality of sensors. In an embodiment, the control unit may be further configured to move randomly or in accordance with a predetermined track until the plurality of sensor signals indicate that the laser beam is received by at least one of the plurality of sensors. For example, the predetermined track can be a track from an end of the movable range of the X-ray detecting unit to the other end.

Figure 7:
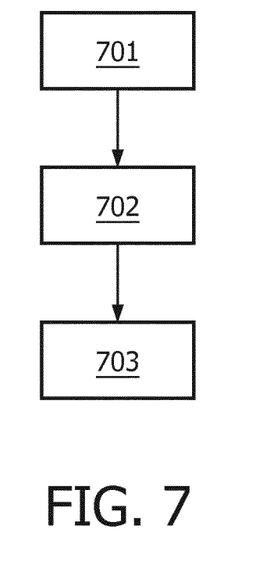
FIG. 7 is a flowchart showing an X-ray imaging method according to an embodiment of the present invention.

FIG. 7 is a flowchart showing an X-ray imaging method according to an embodiment of the present invention.

In step 701, a laser beam La for positioning an X-ray beam to be emitted from an X-ray source unit 101 is emitted, the X-ray source unit 101 comprising an X-ray source for emitting the X-ray beam and a laser adapted to emit the laser beam. The laser beam indicates one or more center positions, along an axis (X), of a region of a subject over which the X-ray beam to be emitted by the X-ray source radiates. The X-ray source unit 101 is adapted to be movable such that the laser beam emitted from the X-ray source unit 101 points at different positions along the X axis during the motion of the X-ray source unit 101. The laser beam is received by a plurality of sensors 104. The plurality of sensors 104 are fixedly disposed in an X-ray detecting unit 102, together with an X-ray detector 12, according to a straight line along the X axis and adapted to be movable together with the X-ray detector 12 along the axis in response to the motion of the X-ray source unit 101.

In step 702, a plurality of sensor signals may be generated by the plurality of sensors 104. Each of the plurality of sensor signals is generated by a corresponding sensor of the plurality of sensors 104. The plurality of sensors 104 comprise a first set of sensors C located at, or adjacent to, a center of the X-ray detector and a second and a third set of sensors L,R located at a first side and a second side, respectively, relative to the center of the X-ray detector.

In step 703, the motion of the X-ray detector along the axis is controlled, based on the plurality of sensor signals. This may be performed by a control unit 105.

The X-ray imaging method may further comprise controlling the X-ray detector 12 to move towards the first side if the plurality of sensor signals indicate that the laser is emitting the laser beam towards the second set of sensors L and to move towards the second side if the plurality of sensor signals indicate that the laser is emitting the laser beam towards the third set of sensors R, and/or controlling the X-ray detector 12 to stop if the plurality of sensor signals indicate that the laser is emitting the laser beam towards the first set of sensors C.

In the case where each of the second and third set of sensors comprises a first subset of sensors HSL, HSR and a second subset of sensors LSL, LSR, respectively, the first subsets of sensors HSL, HSR of the second and third set of sensors are located away from the center of the X-ray detector relative to the second subsets LSL, LSR of sensors of the second and third set of sensors L,R, and the X-ray imaging method further comprises controlling the X-ray detector 12 to move at a first speed if the plurality of sensor signals indicate that the laser is emitting the laser beam towards the first subset of sensors HSL, HSR and at a second speed if the plurality of sensor signals indicate that the laser is emitting the laser beam towards the second subset of sensors LSL, LSR, wherein the first speed is higher than the second speed.

Although it is not shown in FIG. 7, in one embodiment, the X-ray imaging method may comprise comparing each of the plurality of sensor signals with a predetermined threshold to derive comparing results and controlling the motion of the X-ray detector 12 based on the comparing results. In particular, a control signal may be generated based on the comparing results to be output to a motor to drive the motion of the X-ray detector 12.

In a further embodiment, the X-ray imaging method may comprise generating the control signal, based on a comparing result derived by comparing a sensor signal from a second sensor, when two comparing results corresponding to two sensor signals indicate that both magnitudes of the sensor signals from a first sensor and the second sensor are larger than the predetermined threshold, the control signal being generated by switching off a switching circuit to invalidate or disable a comparing result derived by comparing a sensor signal from the first sensor with the first predetermined threshold, wherein the first sensor and the second sensor belong to different sets of sensors located at a same side relative to the center of the X-ray detector 12, and wherein the second sensor is located adjacent to the center of the X-ray detector 12 relative to the first sensor or the second sensor being part of the first set of sensors C located at or adjacent to the center of the X-ray detector 12.

Please note that the X-ray imaging apparatus and method should not be limited to the X-ray imaging apparatus and method mentioned above. It will be apparent to those skilled in the art that the various aspects of the invention claimed may be practiced in other examples that depart from these specific details.

Furthermore, the mere fact that certain measures are recited in mutually different dependent claims does not indicate that a combination of these measures cannot be used to advantage.

It should be noted that the above-mentioned embodiments illustrate rather than limit the invention and that those skilled in the art would be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the product claims enumerating several units, several of these units can be embodied by one and the same item of software and/or hardware. The usage of the words first, second and third, et cetera, does not indicate any ordering. These words are to be interpreted as names.

The invention claimed is:

1. An X-ray imaging apparatus, comprising:
   an X-ray source unit including an X-ray source for emitting an X-ray beam, the X-ray source unit being capable of a translational or rotational movement;
   an X-ray detecting unit comprising an X-ray detector for detecting the X-ray beam, the X-ray detecting unit being capable of the translational movement in order to follow the movement of the X-ray source; and
   a control unit configured to control the movement of the X-ray detecting unit in response to the movement of the X-ray source unit;
   wherein the X-ray source unit further comprises a laser for emitting a laser beam for indicating a center of the X-ray beam;
   wherein the X-ray detecting unit further comprises at least 3 sensors linearly arranged along the translational movement of the X-ray detecting unit, each sensor being configured to sense the laser beam and generate a sensor signal in response to sensing of the laser beam; and wherein the control unit is configured to control the movement of the X-ray detecting unit based on the sensor signal generated by one of the at least 3 sensors.

2. The X-ray imaging apparatus of claim 1, wherein
the at least 3 sensors include a first sensor located at, or adjacent to, a center of the X-ray detector; and
the control unit is configured to stop the movement of the X-ray detecting unit when the laser beam is received by the first sensor.

3. The X-ray imaging apparatus of claim 2, wherein
the at least 3 sensors further include a second sensor and a third sensor located, respectively, at a first side and a second side of the first sensor; and
the control unit is configured to move the X-ray detecting unit towards the first side when the sensor signal is received by the second sensor and to move the X-ray detecting unit towards the second side when the sensor signal is received by the third sensor.

4. The X-ray imaging apparatus of claim 3, wherein
the control unit is configured to control the X-ray detecting unit to move at different speeds.

5. The X-ray imaging apparatus of claim 1, wherein
the control unit comprises at least 3 comparators, each comparator being configured to receive a corresponding sensor signal as a first input and a predetermined threshold as a second input, to compare the corresponding sensor signal with the predetermined threshold, and to output a result of the comparison; and
the control unit is further configured to generate a control signal based on the result of the comparison.

6. The X-ray imaging apparatus of claim 5, wherein the predetermined threshold is a weighted average of magnitudes of the sensor signals.

7. The X-ray imaging apparatus of claim 1, wherein the laser emits the laser beam modulated at a predetermined frequency, and the control unit further comprises a plurality of band filters, each band filter being used for filtering a corresponding sensor signal, and each band filter having a center frequency equal to a predetermined frequency.

8. The X-ray imaging apparatus of claim 1, wherein the at least 3 sensors are arranged on a detector carrier on which the X-ray detector is mounted.

9. The X-ray imaging apparatus of claim 1, wherein the laser is an infrared laser, and the at least 3 sensors are infrared receivers.

10. The X ray imaging apparatus of claim 1, wherein the control unit is further configured to generate a control signal based on the sensor signal, and to output the control signal to a motor for driving the movement of the X-ray detecting unit.

11. The X-ray imaging apparatus of claim 1, further comprising a user interface for outputting an indicating signal if the sensor signal is not received by any of the at least 3 sensors.

12. A method for processing X-ray images, comprising:
emitting an X-ray beam by an X-ray source in an X-ray source unit, wherein the X-ray source unit is capable of a translational or rotational movement;
detecting the X-ray beam by an X-ray detector in an X-ray detecting unit, wherein the X-ray detecting unit is capable of the translational movement in order to follow the movement of the X-ray source; and
control the movement of the X-ray detecting unit by a control unit in response to the movement of the X-ray source unit;
wherein the X-ray source unit further comprises a laser for emitting a laser beam for indicating a center of the X-ray beam;
wherein the X-ray detecting unit further comprises at least 3 sensors linearly arranged along the translational movement of the X-ray detecting unit, each sensor being configured to sense the laser beam and generate a sensor signal in response to sensing of the laser beam; and
wherein the control unit is configured to control the movement of the X-ray detecting unit based on the sensor signal generated by one of the at least 3 sensors.

* * * * *